US012611278B2

(12) United States Patent (10) Patent No.: US 12,611,278 B2

Barker et al. (45) Date of Patent: Apr. 28, 2026

(54) STERILE DRAPE AND APPLICATION METHOD FOR C-arm IMAGING SYSTEMS

(71) Applicant: GE Precision Healthcare LLC, Wauwatosa, WI (US)

(72) Inventors: David Barker, Salt Lake City, UT (US); Ryan Schimpf, Eagle Mountain, UT (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 204 days.

(21) Appl. No.: 18/234,673

(22) Filed: Aug. 16, 2023

(65) Prior Publication Data

US 2025/0057623 A1 Feb. 20, 2025

(51) Int. Cl.
A61B 46/10 (2016.01)
A61B 6/00 (2006.01)

(52) U.S. Cl.
CPC ............ A61B 46/10 (2016.02); A61B 6/4441 (2013.01)

(58) Field of Classification Search
None
See application file for complete search history.

(56) References Cited

U.S. PATENT DOCUMENTS

| | | | |
|---|---|---|---|
| 7,935,100 B2 | 5/2011 | Janus | |
| 8,381,474 B2 | 2/2013 | Lewis | |
| 9,283,041 B2 | 3/2016 | Adams | |
| 10,820,957 B2 | 11/2020 | Turturro et al. | |
| 10,835,337 B2 | 11/2020 | Toure et al. | |
| 11,246,549 B2 | 2/2022 | Matthews | |
| 2004/0059273 A1 | 3/2004 | Worthley | |
| 2004/0112789 A1 | 6/2004 | Robinson | |
| 2011/0041995 A1* | 2/2011 | Adams | A61B 46/13 |
| | | | 156/60 |
| 2014/0084019 A1 | 3/2014 | Cotey | |
| 2015/0124941 A1* | 5/2015 | Arterson | A61B 6/4441 |
| | | | 378/204 |
| 2017/0368302 A1 | 12/2017 | Brooks et al. | |
| 2018/0303693 A1* | 10/2018 | DeSilets | B25J 19/0075 |
| 2019/0142540 A1* | 5/2019 | Chow | A61B 46/10 |
| | | | 428/174 |
| 2021/0128091 A1* | 5/2021 | Youd | A61B 6/462 |
| 2024/0374335 A1* | 11/2024 | Bennaars-Eiden | A61B 46/20 |

FOREIGN PATENT DOCUMENTS

WO 2015110542 A1 7/2015

* cited by examiner

*Primary Examiner* — Marcus H Taningco
(74) *Attorney, Agent, or Firm* — Boyle Fredrickson, S.C.

(57) ABSTRACT

A system and method for attaching a sterile drape to a C-arm of a radiography imaging system includes at least one drape secured to a surface of the C-arm of the radiography system, the at least one drape including a substrate, an attachment strip disposed on the substrate, and a release liner removably attached to the attachment strip opposite the substrate. The substrate includes indica thereon in the form of attachment instructions for the placement of the attachment strip in the proper location on the C-arm. The release liner is removed from the attachment strip and the attachment strip is placed or positioned on the C-arm where indicated by the indicia for properly and quickly attaching the drape to the C-arm. The indica can be located on the release liner, or on the substrate such as on an instruction liner attached to the substrate opposite the attachment strip, or directly on the substrate.

18 Claims, 6 Drawing Sheets

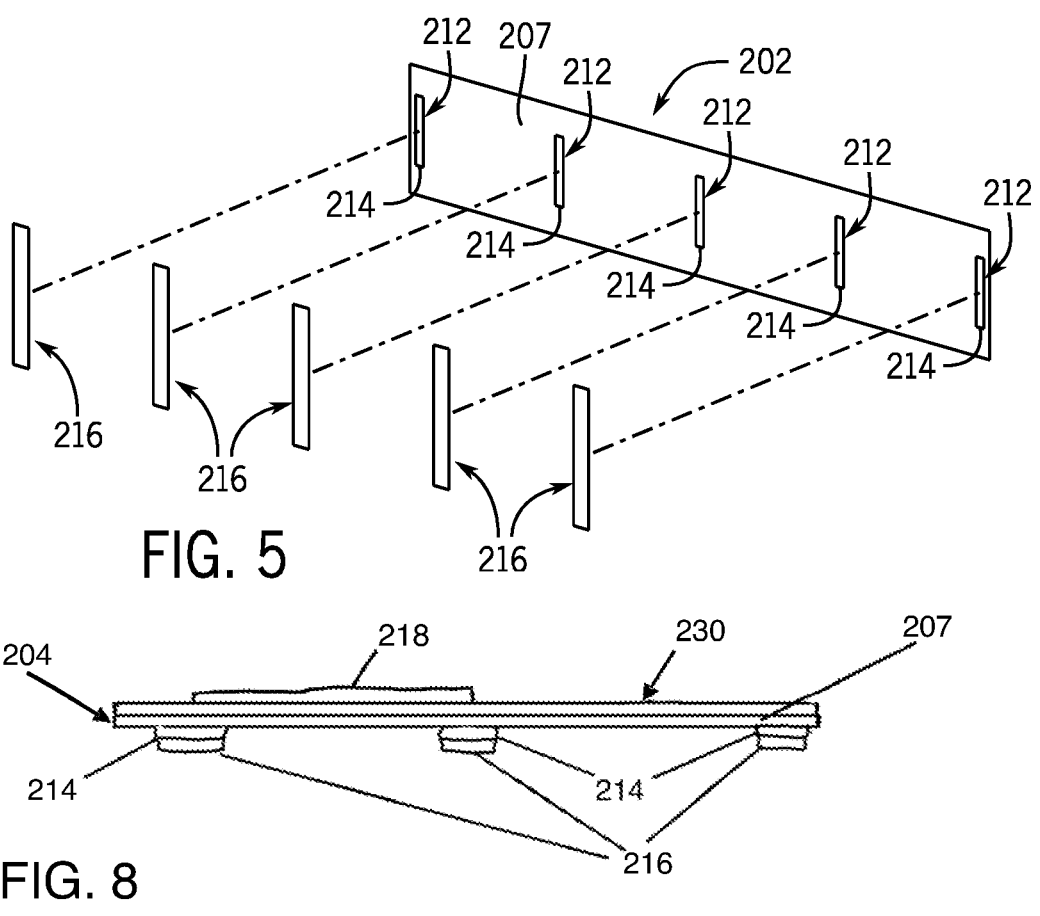
FIG. 5
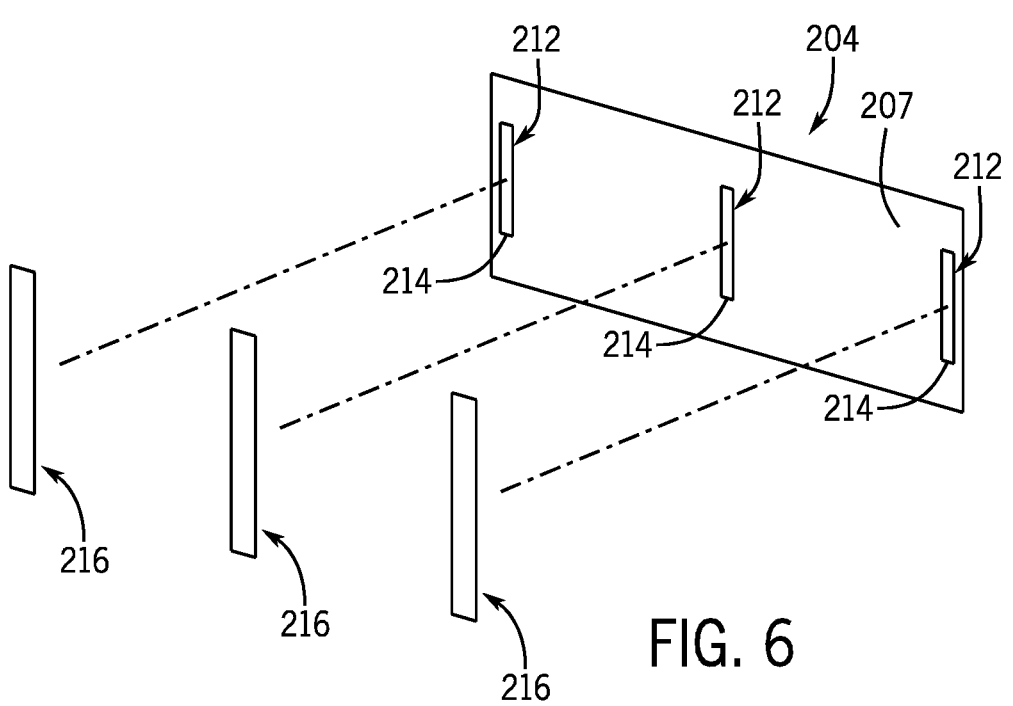
FIG. 8
FIG. 6

STERILE DRAPE AND APPLICATION METHOD FOR C-arm IMAGING SYSTEMS

BACKGROUND OF DISCLOSURE

The subject matter disclosed herein relates to X-ray imaging systems having C-arms and, more particularly, to sterile drapes and application methods for use with C-arm X-ray imaging systems.

Medical diagnostic and surgical or surgery imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic and/or surgical imaging equipment has been developed. The term C-arm generally refers to an X-ray imaging system or device having a rigid and/or articulating structural member having an X-ray source and an image X-ray detector assembly that are each located at an opposing end of the structural member so that the X-ray source and the image X-ray detector face each other. The structural member is typically "C" shaped and so is referred to as a C-arm. In this manner, X-rays emitted from the X-ray source can impinge on the image detector and provide X-ray image data/X-ray images of the object or objects that are placed between the X-ray source and the image detector.

In many cases, C-arms are connected to one end of a movable arm disposed on a base or gantry. In such cases, the C-arm can often be raised and lowered, be moved from side to side, and/or be rotated about one or more axes of rotation via the moveable arm. Accordingly, such C-arms can be moved and reoriented to allow X-ray images to be taken from several different positions and angles and different portions of a patient, without requiring the patient to be frequently repositioned.

The processes that involve the use of the C-arm X-ray imaging system are often performed in an operating room where it is important to maintain sterility, and the area above the waist where the operation is being performed. As the C-arm X-ray imaging system can be employed in multiple procedures in a single day, due to the large number of surfaces present on the C-arm and the movement of the C-arm into many different positions during the performance of a single operation, it is difficult to provide adequate sterilization to the C-arm imaging system itself.

In order to provide a more suitable system and method for enabling the use of the C-arm imaging system in a sterile environment, such as an operating room, a number of prior art drape systems have been developed. Referring to FIG. 1, one prior art drape system includes a large bag 1000 formed of a plastic material that is disposed over the detector 1002 and a portion of the C-arm 1004, or that only covers the detector 1002 with another independent drape 1006 for the C-arm 1004. With these prior art drapes, the large bag 1000 is held in position over the C-arm 1004 and/or the detector 1002 by elastic or tape strips 1008 that are wrapped around the C-arm 1004 and/or portions of the detector 1002. Further, prior art drapes including an independent C-arm drape 1006 employ a custom frame and/or rods 1010 disposed on/attached to the C-arm 1004 that are engaged by clips and/or an adhesive 1012 disposed on the drape 1006 in order to secure the drape 1006 to the C-arm 1004, as shown in FIG. 2. With these drape systems, the plastic material forming the bag 1000 and drapes 1006 surrounding the detector 1002 and C-arm, prevents direct contact with detector 1002 and/or C-arm 1004. But in all cases, no drape has clear attached instructions that guide or direct the installation of the drape onto the system.

However, these prior art drape systems have some significant drawbacks regarding their implementation on C-arm imaging systems. For example, it is impractical to use the bag 1000 and/or the drape 1006 secured with the elastic or tape strips 1008, as when the C-arm 1004 is repositioned, the extra material forming the bag 1000 and/or drape 1006 will bunch up, tear, or restrict the motion of the C-arm 1004. Further, with regard to the drapes 1006 for specific attachment directly to the C-arm 1004, the clips 1012 must attach in at least two locations on the C-arm 1004, i.e., on the same side or opposed sides of the C-arm 1004, making it difficult for an individual to hold the entire drape 1006 and get the clips 1012 to engage the rods 1010 correctly on the C-arm 1004.

In addition, these prior art drape systems do not have instructions on the bag 1000 and/or drape 1006 to assist the user in properly locating each strip 1008 or clip 1012. As such, the installation of the bag 1000 and or drape 1006 is a trial and error process, even when the individual installing the bag 1000 and/or drape 1006, as well as the supporting frame or rods 1010, has experience in doing so, thus making the installation process time consuming and inconsistent, which is not desirable for an operating environment where time can be of the essence.

Therefore, it is desirable to develop an improved sterile drape system and installation method for a C-arm X-ray imaging system that provides an improved manner of properly positioning the drape on the C-arm imaging system with minimal time and effort.

BRIEF DESCRIPTION OF THE DISCLOSURE

According to one exemplary non-limiting aspect of the disclosure, a sterile drape system for a C-arm of a radiography imaging system includes a first sterile drape having a first substrate formed of a flexible plastic material, at least one first attachment strip disposed on the first substrate, and at least one first release liner removably attached to the at least one first attachment strip opposite the first substrate, the first substrate including indica thereon in the form of attachment instructions for the placement of the at least one first attachment strip on the C-arm.

According to another exemplary non-limiting aspect of the disclosure, a radiography imaging system includes a base, a C-arm movably connected to the base, the C-arm including the x-ray source and the detector disposed thereon, and at least one drape secured to a surface of the C-arm of the radiography imaging system, the at least one drape having a substrate, at least one attachment strip disposed on the substrate, and at least one release liner removably attached to the at least one attachment strip opposite the substrate, the substrate including indica thereon in the form of attachment instructions for the placement of the at least one attachment strip on the C-arm.

According to still another aspect of one exemplary non-limiting embodiment of the disclosure, a method for attaching a sterile drape to a C-arm of a radiography imaging system includes the steps of providing at least one drape secured to a surface of the C-arm of the radiography imaging system, the at least one drape including a substrate, at least one attachment strip disposed on the substrate, and at least one release liner removably attached to the at least one attachment strip opposite the substrate, the substrate including indica thereon in the form of attachment instructions for the placement of the at least one attachment strip on the C-arm, removing the at least one release liner from the at least one attachment strip. and placing the at least one attachment strip on the C-arm where indicated by the indicia.

It should be understood that the brief description above is provided to introduce in simplified form a selection of concepts that are further described in the detailed description.

BRIEF DESCRIPTION OF THE DRAWINGS

The drawings illustrate the best mode presently contemplated of carrying out the disclosure. In the drawings:

FIG. 5 is an isometric view of the improved drape system of FIG. 4 according to one exemplary non-limiting embodiment of the disclosure.

FIG. 6 is an isometric view of the improved drape system of FIG. 4 according to another exemplary non-limiting embodiment of the disclosure.

FIG. 8 is a cross-sectional view of the drape system of FIG. 4 in accordance with another exemplary embodiment of the disclosure.

DETAILED DESCRIPTION

Figures 1, 2:
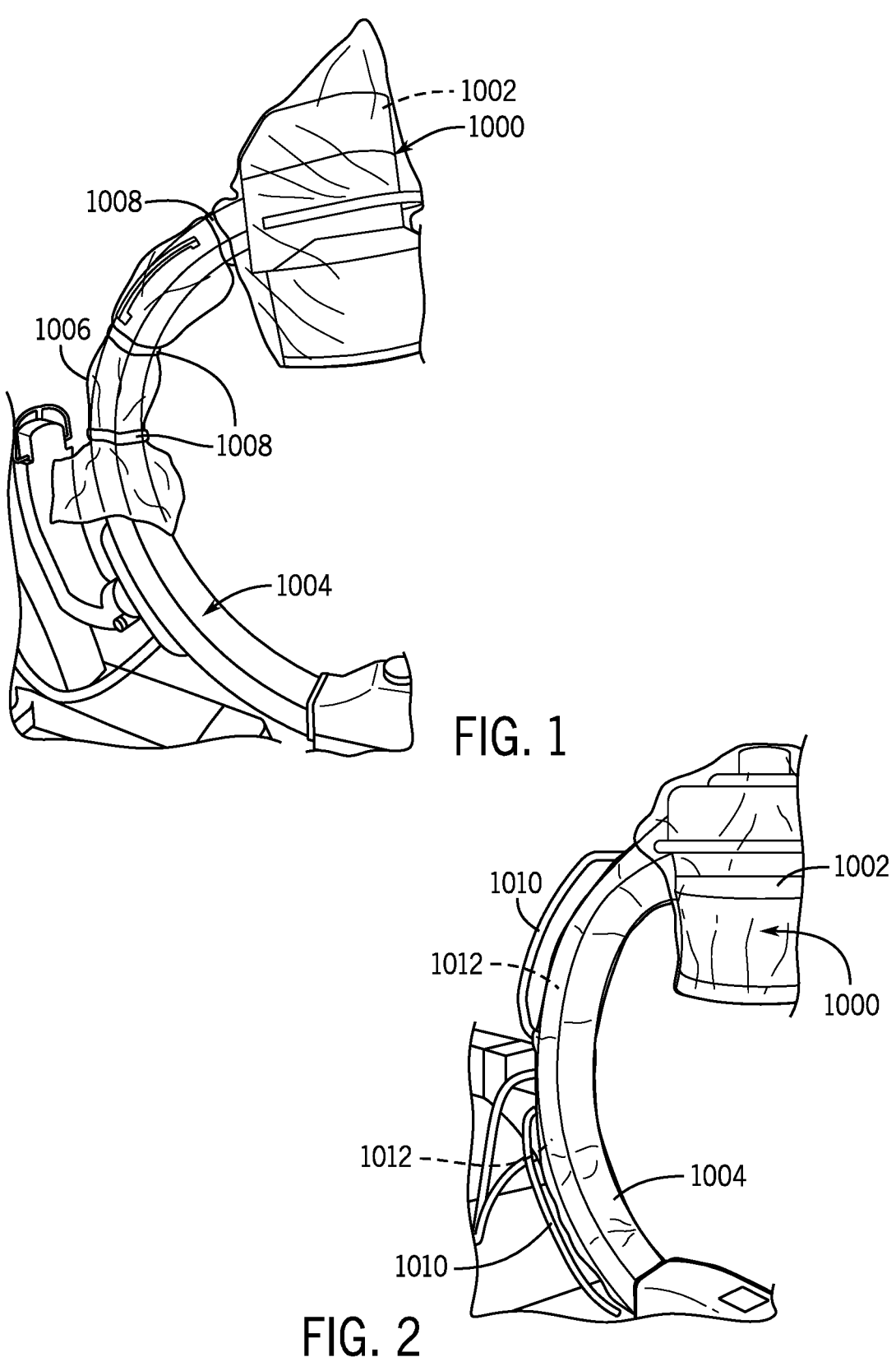
FIG. 1 is a perspective view of a first prior art drape system secured to a C-arm imaging system.
FIG. 2 is a perspective view of a second prior art drape system secured to a C-arm imaging system.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Medical imaging systems may include a C-shaped arm that carries a radiation source and a radiation detector. The C-shape of the arm allows a physician to access to a patient while the patient is being imaged. In order to obtain medical images of an internal structure at various angles, the C-shaped arm may be rotated to various positions. The following description relates to various embodiments for a medical imaging system with a C-arm. A medical imaging system, such as the medical imaging system shown in FIG. 1, includes a C-arm configured to rotate around at least one rotational axis. The C-arm includes a radiation source and a radiation detector at opposite ends of the C-arm.

Referring to the figures generally, the present disclosure describes systems and methods for a medical imaging system with a C-arm. The medical imaging system described herein (i.e., the medical imaging system depicted in FIG. 3) may be generally referred to as a radiography imaging system, and in particular a mobile C-arm imaging system.

Figure 3:
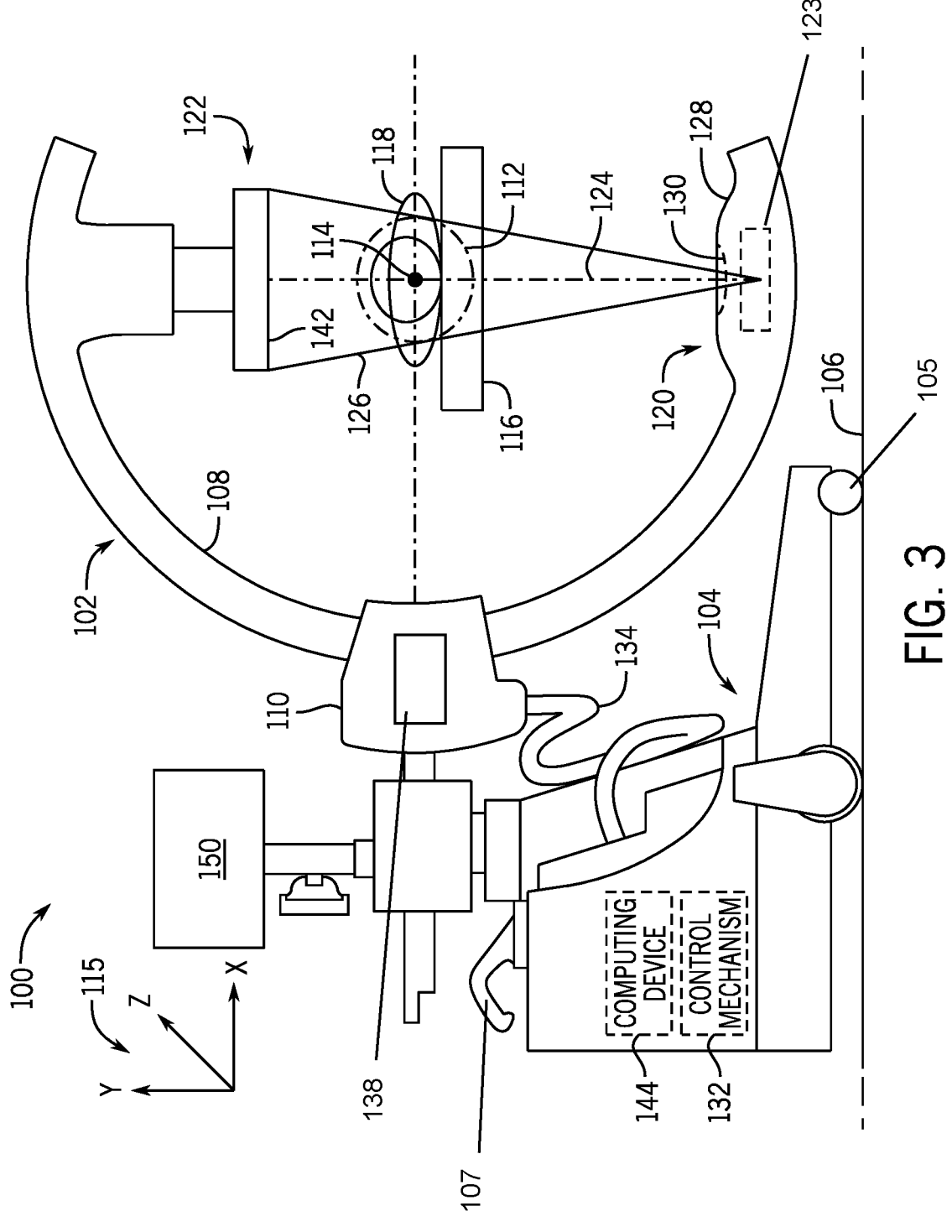
FIG. 3 is a side elevation view of a radiography imaging system including a C-arm according to one exemplary non-limiting embodiment of the disclosure.

Referring now to FIG. 3, a medical radiography imaging system 100, such as that disclosed in US Published Patent Application Serial No. US2022/0401048, entitled *Imaging System With Carbon Fiber C-Arm*, the entirety of which is expressly incorporated herein by reference for all purposes, is shown in accordance with an exemplary embodiment. The radiography imaging system 100 includes a rotatable C-arm 102 that is connected to a base 104. The base 104 supports the C-arm 102 while the C-arm 102 is stationary and while rotating. The base 104 supports the C-arm 102 on a ground surface 106 on which the radiography imaging system 100 sits via a number of wheels 105 or similar rotatable supports that enable the base 104 to be readily moved over and/or along the surface 106 by an operator, such as by grasping handles 107 on the base 104 and pulling or pushing the radiography imaging system 100 into the desired position for the operation of the radiography imaging system 100. The C-arm 102 includes a C-shaped portion 108 that is connected to an extended portion 110. The extended portion 110 is rotatably coupled to the base 104 which allows the C-arm 102 to rotate about an examination region 112 and a rotational axis 114. For example, the C-arm 102 may be configured to rotate at least 180° in opposing directions relative to the base 104, though in some embodiments, the C-arm 102 may be configured to rotate at least 220°. Configuring the C-arm 102 to rotate at least +/−100° may provide a physician with greater access to a patient being imaged. While the following describes the rotation of the C-arm 102 as rotating in the X and Y directions of the Cartesian coordinate system 115 (i.e., rotating the C-shaped portion 108 such that opposing ends of the C-shaped portion 108 are closer to or further from the extended portion 110 in various positions), it is understood that the C-arm 102 may also rotate in the Z direction (i.e., rotating the C-shaped portion 108 such that opposing ends of the C-shaped portion 108 are closer to or further from a head of the patient within the examination region 112 in various position and/or changing the elevation of the extended portion 110 relative to the base 104 employing a suitable vertical translation mechanism (not shown) disposed on the base 104 and engaged with the extended portion 110.

The radiography imaging system 100 further includes a patient support 116 (i.e., couch, bed, table, etc.) that supports an object or patient, such as a patient 118 while at least a portion of the patient 118 is within the examination region 112. The radiography imaging system 100 additionally includes a radiation source 120 and a radiation detector 122. The radiation source 120 and the radiation detector 122 are supported by and rotate with the C-arm 102. Furthermore, the radiation source 120 and the radiation detector 122 are positioned at opposite ends of the C-shaped portion 108 of the C-arm 102 along axis 124, where axis 124 intersects and extends radially relative to the rotational axis 114. The C-shaped portion 108 may be rotated as described above in order to adjust the position of the radiation source 120 and the radiation detector 122 to obtain 2D projection images of the patient 118 at each selected orientation of the radiation source 120 relative to the radiation detector 122 in order to form a 2D projection dataset. Furthermore, in the embodiment depicted in FIG. 1, the position of the radiation detector 122 may be varied such that the radiation detector 122 is placed further from or closer to the radiation source 120.

During a medical imaging procedure, a portion of the patient 118 is within the examination region 112 and the radiation source 120 emits radiation 126. In one embodiment, the radiation source 120 may include an X-ray tube 123 housed within a casing 128. The X-ray tube generates the radiation 126 which escapes the casing 128 via an outlet 130. The radiation 126 traverses the examination region 112 and is attenuated by the portion of the patient 118 that is within the examination region 112. Specifically, the radiation source 120 emits the radiation 126 towards the radiation detector 122 which is on the opposite end of the C-arm 102. The radiation source 120 emits cone-shaped radiation which is collimated to lie within an X-Y-Z plane of the Cartesian coordinate system 115 which is generally referred to as an "object plane" which is parallel to the radiation detector 122 at an isocenter of the C-arm 102.

After passing through a portion of the patient 118, the attenuated radiation is captured by the radiation detector 122. In some embodiments, the radiation detector 122 includes a plurality of detector elements (not shown) that acquire projection data. Each detector element produces an electrical signal that is a measurement of the attenuation at the detector element location. The attenuation measurements from all the detector elements in the radiation detector 122 are acquired separately to produce a transmission profile. In one embodiment, the radiation detector 122 is fabricated in a flat panel configuration including a plurality of detector elements.

When the radiation source 120 and the radiation detector 122 are rotated with the C-arm 102 within the object plane and around the patient 118, the angle at which the radiation 126 intersects the patient 118 changes. A group of attenuation measurements (i.e., projection data) form the radiation detector 122 at one C-arm angle is referred to a "view." A "scan" of the patient 118 includes a set of projection views made at different angles, or view angles, during rotation of the C-arm 102. As used herein, the term view is not limited to the use described herein with respect to projection data obtained from or from one C-arm 102 angle. The term view is used to mean one data acquisition whenever there are multiple acquisitions from different angles, such as used to form the 2D projection dataset.

The radiography imaging system 100 further includes a control mechanism 132 that is housed within the base 104. The control mechanism 132 is connected to the C-arm 102, the radiation source 120, and the radiation detector 122 via a cable 134 which allows the control mechanism to send data to/receive data from the C-arm 102, the radiation source 120, and the radiation detector 122. The control mechanism 132 controls the rotation of the C-arm 102 and the operation of the radiation source 120. While FIG. 1 depicts the base 104 as including the control mechanism 132, in other embodiments the control mechanism may be separate from the base 104 (i.e., in a different room).

The C-arm 102 may be adjusted to a plurality of different positions by rotation of the C-shaped portion 108. For example, in an initial, first position shown by FIG. 1, the radiation detector 122 may be positioned vertically above the radiation source 120 relative to the surface 106 on which the radiography imaging system 100 sits, with axis 124 arranged normal to the surface 106 intersecting a midpoint of the outlet 130 of the radiation source 120 and a midpoint of a detector surface 142 of the radiation detector 122. The C-arm motor controller 138 and a guide system within the extended portion 110 may adjust the C-shaped portion 108 from the first position to a different second position by rotating the C-shaped portion 108 via a coupling between the guide system and the C-shaped portion 108. In one example, the second position may be a position in which the radiation source 120 and the radiation detector 122 are rotated 180° together relative to the first position such that the radiation source 120 is positioned vertically above the radiation detector 122, with the axis 124 intersecting the midpoint of the outlet 130 of the radiation source 120 and the midpoint of the detector surface 142 of the radiation detector 122. When adjusted to the second position, the radiation source 120 may be positioned vertically above the rotational axis 114 of the C-shaped portion 108 and the radiation detector 122 may be posited vertically below the rotational axis 114.

The radiography imaging system 100 further includes a computing device 144 that is housed within the base 104 that is operable to generate images for presentation on a display 150. While FIG. 1 depicts the computing device 144 as housed within the base 104, in other embodiments the computing device 144 may be remote from the rest of the radiography imaging system 100. As used herein, a computing device (or system) is any device/system capable of processing, storing, and/or transmitting data (i.e., tablet, handheld device, smartphone, personal computer, laptop, network computer, server, mobile communication device, etc.). The computing device 144 may be connected to a network (i.e., a wide area network (WAN), a local area network (LAN), a public network (the internet), etc.) which allows the computing device 144 to communicate with other devices on a same network. In some embodiments, the network may be regarded as a private network and may include, for example, a virtual private network.

Figure 4:
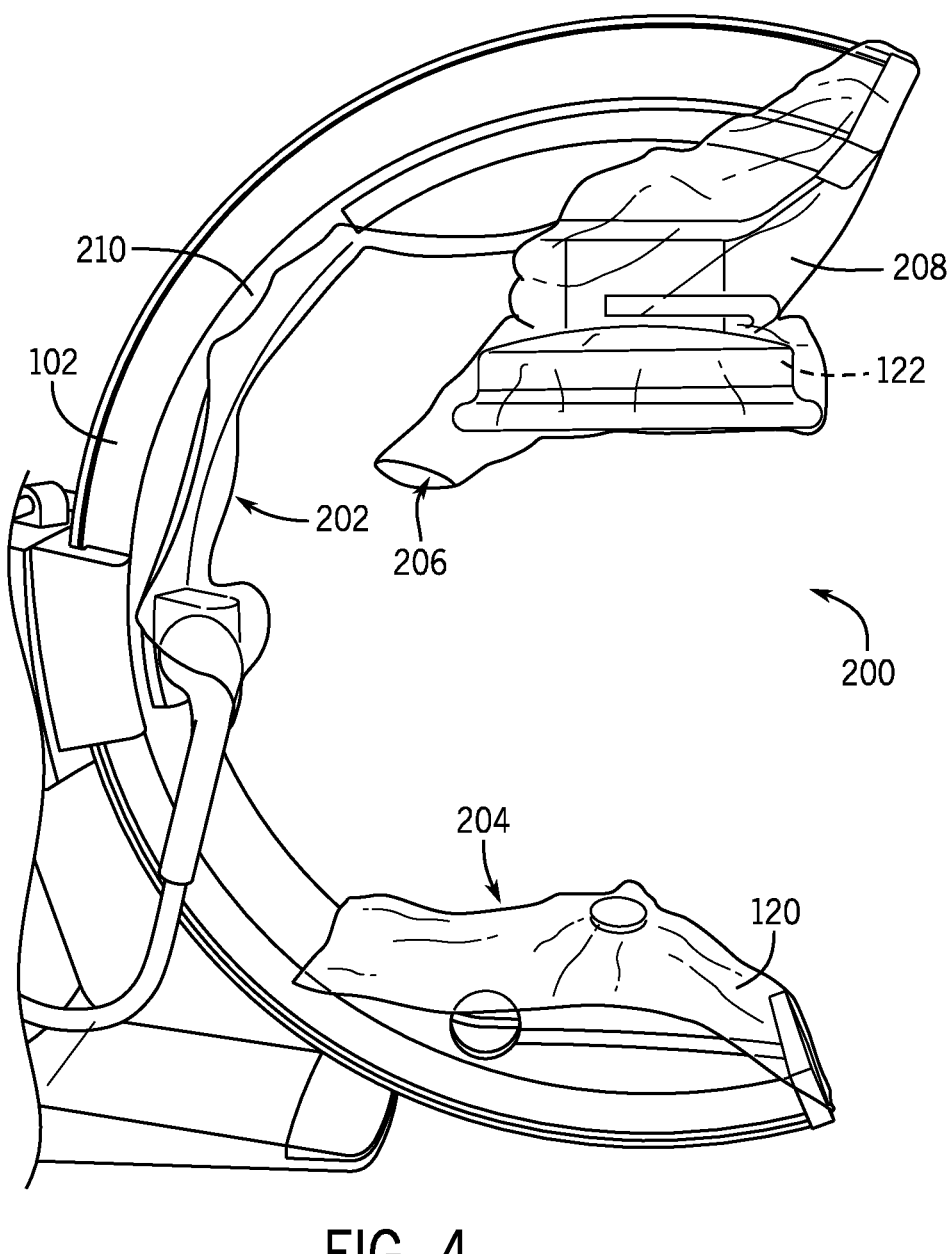
FIG. 4 is a side elevation view of the radiography imaging system of FIG. 1 including the improved drape system according to one exemplary non-limiting embodiment of the disclosure secured thereto.
Figures 7A, 7B, 7C:
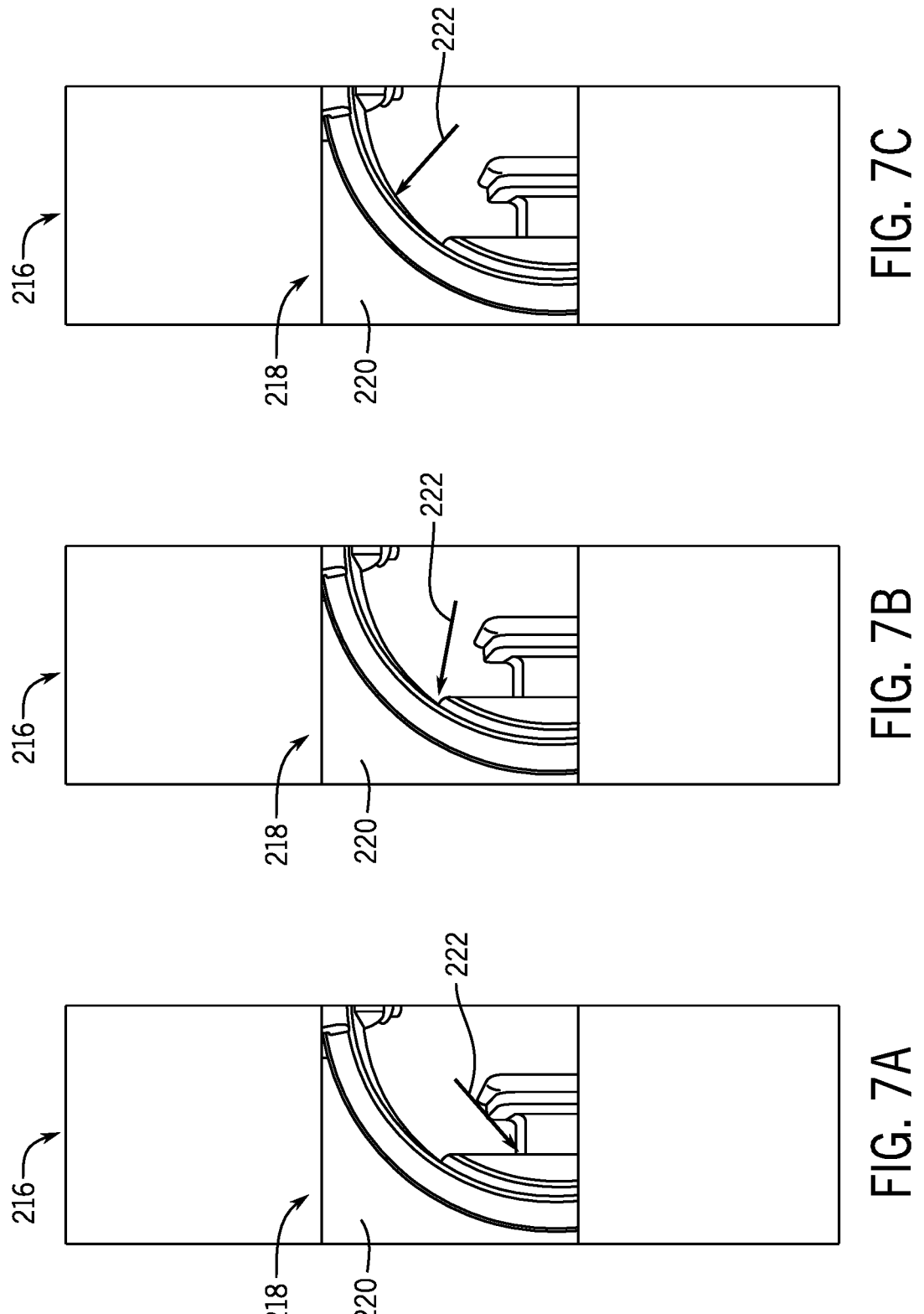
FIGS. 7A-7E are top plan view of release liners including graphical instructions for locating adhesive strips covered by the release liners on the C-arm of the radiography imaging system according to another exemplary embodiment of the disclosure.
Figures 7D, 7E:
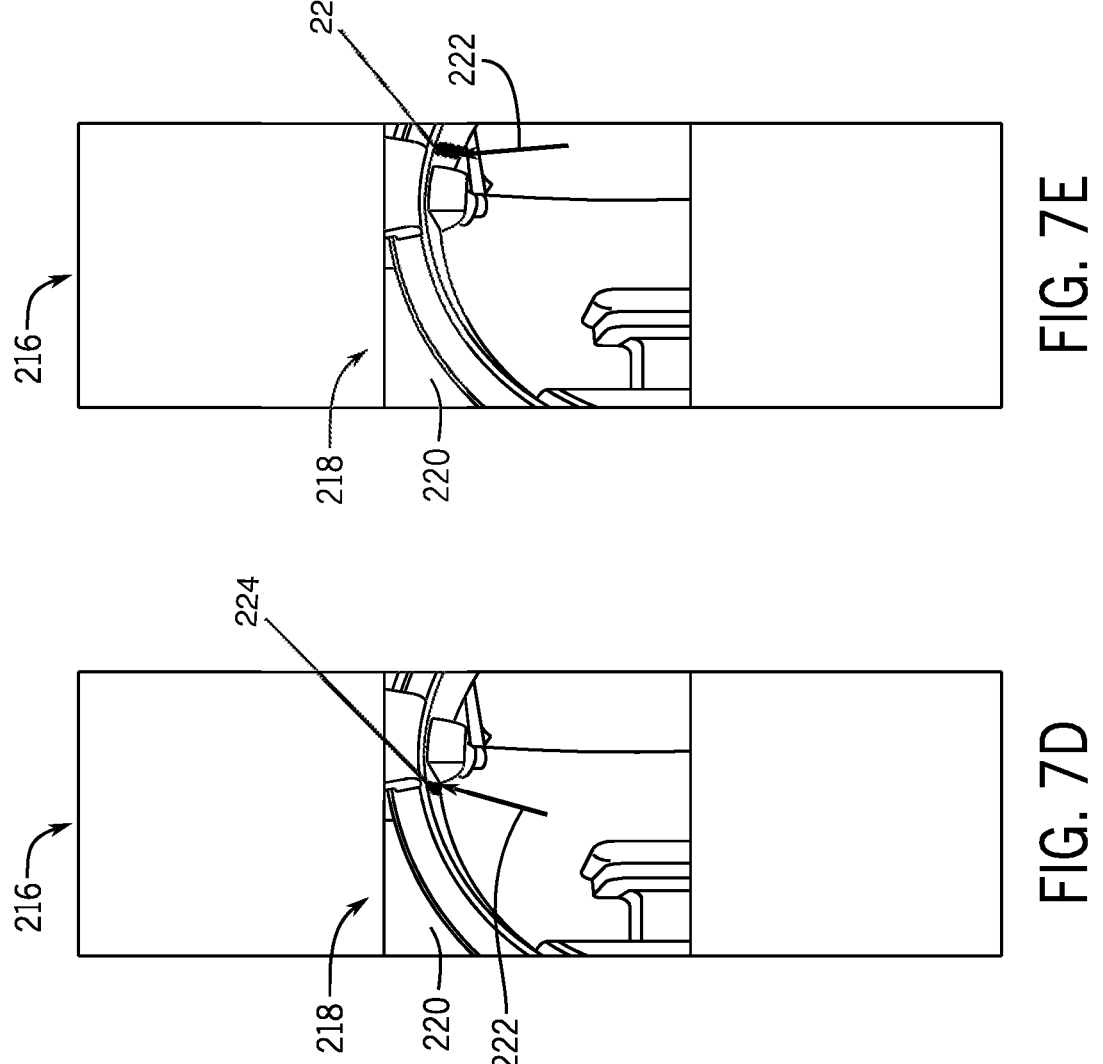

Turning to FIG. 4, the radiography imaging system 100 includes a drape system 200 positioned thereon. The drape system 200 can include one or more individual sterile drapes 202,204,206 that are attachable to the C-arm 102, the radiation source 120 and/or the radiation detector 122. Each sterile drape 202,204,206 is formed with a substrate 207 (FIG. 5) of a suitable flexible plastic material, such as a transparent plastic material including but not limited to a polyethylene film. To assist on covering the associated surface, the plastic material forming the sterile drapes 202, 204,206 can also be formed with a thickness greater than that of prior art drapes, i.e., of approximately 4 mm or greater thickness, which is double the thickness of prior art drapes. This thickness is useable for the drapes 202,204,206 as the size, location and attachment structures (to be discussed) of the drapes 202,204,206 eliminates the bunching, twisting and stretching issues present in the prior art drapes.

In one exemplary embodiment, the drape 206 formed to be positioned over the radiation detector 122 can be formed with any suitable shape, and in the exemplary illustrated embodiment has a three-dimensional shape that defines an interior 208 within which the radiation detector 122 can be positioned. As best shown in FIG. 4, the drape 206, encloses the radiation detector 122 and is secured to the C-arm 102 and/or the radiation detector 122 in a suitable manner to retain the drape 206 in the desired positioned around the radiation detector 122 during use of the radiography imaging system 100 in the sterile environment. With this configuration, the drape 202,204,206 can be placed in the appropriate location on the C-arm 102 using only a single hand of the individual attaching the drape 202,204,206, and/or without the need for any additional securing structures, such as rods, rails, clips or elastics operably engaged with the C-arm 102 and/or the drape 202,204,206.

The drape 202 positioned along the C-arm 102 and the drape 204 disposed over the radiation source 120 can also be formed with any suitable shape, such as a shape that conforms to the shape of the portion of the C-arm 102 to which the drape 202 is to be attached, but in the illustrated exemplary embodiment of FIGS. 4-6, the drapes 202,204, as well as optionally the drape 206 positioned on the radiation detector 122, are each formed as a thin, planar sheet with a rectangular shape. The selected length of the drape 202,204 is sufficient to extend along the entire surface of the C-arm 102 to cover the surface 210 of the C-arm 102 facing the patient 118. With the rectangular shape, the drapes 202,204 provide a suitable a barrier to prevent contact of the C-arm 102 and/or the radiation source 120 with any sterile surface or object in the area surrounding the radiography imaging system 100, e.g., within an operating room or theater. Further, the rectangular shape of the drapes 202 and/or 204 defines an area that is sufficient to cover the C-arm surface 210 and the radiation source 120, but does not extend to cover the opposed sides of the C-arm 102 or the radiation source 120. In this construction the drapes 202,204 only use the necessary amount of material required to cover the exposed surfaces of the radiography imaging system 100 most likely to be contacted during the use of the radiography imaging system 100 in the sterile environment, thereby minimizing waste generated by the drape system 200.

With the potential for the drapes 202,204 and/or 206 forming the drape system 200 to have similar shapes, in an exemplary embodiment for the drape system 200 where each of the C-arm drape 202 and the source drape 204 are present and rectangular in shape, the drapes 202,204,206 can each be formed with identifying characteristics that allow for clear identification and/or determination of the drapes 202,

204,206 from one another. In one exemplary embodiment of these identifying characteristics, the drapes 202,204,206 can be formed with transparent plastic materials having different colors or tints, while maintaining the transparency of the materials forming the drapes 202,204,206.

Referring now to FIGS. 5-7E, in order to attach one or more of the drapes 202,204,206 to the radiography imaging system 100, the drapes 202,204,206 include a number of attachment strips 212 disposed on each drape 202,204,206. The attachment strips 212 in the illustrated exemplary embodiment take the form of adhesive strips 214 formed of an adhesive that can be applied, removed and re-applied to a surface to secure the drapes 202,204,206 to the surface. In one particular exemplary embodiment, the adhesive strips 214 are formed of an acrylic adhesive that can readily be affixed to a plastic material utilized to form the drapes 202,204,206 of the drape system 200. In an exemplary embodiment, the adhesive strips 214 are formed to be opaque or translucent, but not transparent, in order to allow the adhesive strips 214 to be readily seen through the drape 202,204,206 and properly placed on the appropriate surface of the radiography imaging system 100. While the exemplary illustrated embodiment shows the adhesive strips 214 formed with a continuous length of the adhesive, other configurations are also contemplated to reduce the amount of adhesive required to attach the drape 202,204,206 to the radiography imaging system 100, such as adhesive strip 214 formed with one or more spaced adhesive spots (not shown), or an adhesive line (not shown) around the perimeter of the adhesive strip 214 but defining an open center therein (not shown). Further, while the illustrated exemplary embodiments in FIGS. 5 and 6 show five (5) and three (3) adhesive strips 214 spaced from one another in a parallel orientation on the drape 202,204,206, respectively, any number of adhesive strips 214 can be employed on the individual drapes 202,204,206, and in any configuration. For example, the adhesive strips 214 can be disposed in various numbers and orientations on the individual drapes 202,204,206, and can have different shapes and/or positions in order to accommodate for the shapes and/or contours of the different surfaces to which the drapes 202,204,206 are secured on the C-arm 102, the radiation source 120 and the radiation detector 122, respectively.

To prevent the premature adherence of the adhesive strips 214 to a surface, such as the surface 210, the adhesive strips 214 are each covered by a release liner 216. The release liner 216 is formed from a material that is readily adherable to the adhesive strip 214 but that can also be readily removed from the adhesive strip 214. In one exemplary embodiment of the invention the release liner 216 is formed of a paper or plastic substrate coated on at least one side with a silicone material coating to enable the substrate to be removed from the adjacent adhesive strip 214.

Each liner 216 also includes indicia 218 formed and/or printed thereon. As shown in each of FIGS. 7A-7E, the indicia 218 provides information in the nature of installation instructions for the attachment of the associated drape 202,204 and/or 206 to the C-arm 102, the radiation source 120 and/or the radiation detector 122. In the particular illustrated exemplary embodiment, the indicia 118 is a location image 220, e.g., a schematic or picture, of a portion of the radiography imaging system 100, such as the C-arm 102 and/or the radiation detector 122 and a location icon or arrow 222 identifying and/or pointing towards a particular location on the C-arm 102, the radiation source 120, and/or the radiation detector 122. Thus, the location image 220 illustrates the particular location on the radiography imaging system 100 where the adhesive strip 214 associated with the location image 220 on the attached release liner 216 is to be placed. Thus, the instructions provided by the indica 218/ location image 220 enable a precise placement of the selected attachment strip 212/adhesive strip 214 on the appropriate surface of the radiography imaging system 100 to allow for quick and easy positioning of the drape 202,204 and/or 206 on the radiography imaging system 100. While the location image 220 illustrated in the exemplary embodiment of FIGS. 7A-7E shows a side view of the C-arm 102 and radiation detector 122, other views can be used as substitutions for, or in conjunction with the side view location image 220, including a top view (not shown) of the surface to which the attachment strip 212/adhesive strip 214 is to be attached, along with an indication (not shown), such as a solid icon (e.g., strip of rectangle) showing the location for the proper placement of the attachment strip 212/adhesive strip 214 on the surface 210. Further, while the illustrated exemplary embodiments of FIGS. 7A-7E show the indicia 218 as being formed of the location image 220 and the location icon 222, the indicia 218 can also include text or a graphic representation 224 describing the location for the attachment strip 212/adhesive 214. This text can be located adjacent the location image 220 and location icon 222 to provide a written indication of the proper location of the attachment strip 212/adhesive strip 214 on the radiography imaging system 100. Additionally, the location image 220, the location icon 222, and the text can be employed as the indicia 218 in any combination to provide a readily discernable indication of the proper location for the strip 212/214 associated with the release liner 216 on which the particular indicia 218 is disposed. As the drape 202,204,206 can be supported on the C-arm 102 by a single attachment strip 212/adhesive strip 214, all subsequent or additional attachment strips 212/adhesive strips 214 can be secured to the appropriate locations on the C-arm 102 using a single hand, with a single pressing motion to attach the attachment strip 212/adhesive strip 214 to the selected surface of the C-arm 102, and without the need for any additional securing structures, e.g., clips, rods, rails and/or elastic bands.

By using the re-attachable attachment strips 212/adhesive strips 214 and the instruction indicia 218 presented on the release liners 216 for each attachment strip 212/adhesive strip 214 on the drapes 202,204,206, the user of the drape system 200 can quickly and easily place the selected drape 202,204,206 in the correct position on the radiography imaging system 100. The use of the indicia 218 on the release liners 216 provides a significant reduction in the cost for the drape system 200 in comparison to prior art drapes as a result of the elimination of the clips and rods and/or frames previously necessary to secure drapes to the C-arm 102 of the radiography imaging system 100. Also, the reduction in the size and/or area of the individual drapes 202,204,206 formed as a flat sheet to cover surfaces, such as only those non-sterile surfaces on the radiography imaging system 100, that are located within a sterile field defined by the sterile environment in which the radiography imaging system 100 is positioned, e.g., above waist height in the sterile environment, and that are often contacted additionally reduces the cost for the drapes 202,204,206.

In an alternative embodiment shown in FIG. 8, the one or more of the drapes 202,204,206 on the drape system 200 can additionally include an instruction liner 230 disposed on the drape 202,204,206 in any suitable manner, an optionally configured to remain attached to the drape 202,204,206 when in use, e.g., be permanently attached to the drape 202,204,206. The indicia 218 can be printed or otherwise presented on the instruction liner 230 to be viewable by the user when placing the drape 202,204,206 on the radiography imaging system 100 in the location identified by the indicia 218 on the instruction liner 230. Further, in still another embodiment, the instruction liner 230 can be omitted and the indicia 218 can be printed or otherwise presented directly on the surface of the drape 202,204,206 opposite the attachment strips 212/adhesive strips 214 and release liners 216.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sterile drape system for a radiography imaging system including a C-arm, the drape system comprising a first sterile drape comprising:
   a. a first substrate formed of a flexible plastic material;
   b. at least one first attachment strip disposed on the first substrate; and
   c. at least one first release liner removably attached to the at least one first attachment strip opposite the first substrate, the first substrate including indica thereon in the form of attachment instructions for the placement of the at least one first attachment strip on the C-arm,
   wherein the indica comprises:
   a. a location image of the C-arm; and
   b. a location icon identifying a location on the C-arm picture for proper placement of the at least one first attachment strip.

2. The sterile drape system of claim 1, wherein the first substrate is formed of a transparent flexible plastic material.

3. The sterile drape system of claim 1, wherein the at least one first attachment strip is formed of a non-transparent adhesive.

4. The sterile drape system of claim 1, further comprising a second sterile drape, the second sterile drape comprising:
   a. a second substrate formed of a flexible plastic material;
   b. at least one second attachment strip disposed on the second substrate; and
   c. at least one second release liner removably attached to the at least one second attachment strip opposite the second substrate, the second substrate including indica thereon in the form of attachment instructions for the placement of the at least one second attachment strip on the C-arm.

5. The sterile drape system of claim 4, wherein the first substrate is formed with a first color, and the second substrate is formed with a second color.

6. The sterile drape system of claim 5, wherein the first color is different from the second color.

7. The sterile drape system of claim 1, wherein the indicia is disposed on the at least one release liner.

8. The sterile drape system of claim 1, further comprising an instruction liner attached to the first substrate opposite the at least one first attachment strip, the indicia presented on the instruction liner.

9. The sterile drape system of claim 1, wherein the first sterile drape comprises:

a. a number of first attachment strips disposed on the first substrate and spaced from one another; and b. a number of first release liners, each first release liner removably attached to an associated first attachment strip opposite the first substrate, each first release liner including indica thereon comprising:

i. a location image of the C-arm; and ii. a location icon identifying a location on the C-arm within the location image for proper placement of the associated first attachment strip.

10. The sterile drape system of claim 1, wherein the first substrate is formed as a planar sheet of the flexible plastic material.

11. A radiography imaging system comprising:

a. a base;

b. a C-arm movably connected to the base, the C-arm including the x-ray source and the detector disposed thereon; and c. at least one drape secured to a surface of the C-arm radiography system, the at least one drape comprising:

i. a substrate;

ii. at least one attachment strip disposed on the substrate; and iii. at least one release liner removably attached to the at least one attachment strip opposite the substrate, the at least one release liner including indica thereon in the form of attachment instructions for the placement of the at least one attachment strip on the C-arm, wherein the indica comprises:

a. a location image of the C-arm; and b. a location icon identifying a location on the C-arm within the location image for proper placement of the at least one attachment strip.

12. The imaging system of claim 11, wherein the at least one drape is attached to a non-sterile surface of the C-arm located within a sterile field defined in a sterile environment within which the imaging system is positioned.

13. The imaging system of claim 11, further comprising:

a. a first drape attached to the C-arm between the detector and the source; and b. a second drape attached to the detector.

14. The imaging system of claim 13, wherein the substrate of the first drape has a color different than a color of the substrate of the second drape.

15. A method for attaching a sterile drape to a C-arm of a radiography imaging system, the method comprising the steps of:

a. providing at least one drape to be secured to a non-sterile surface of the C-arm, the at least one drape comprising:

i. a substrate;

ii. at least one attachment strip disposed on the substrate; and iii. at least one release liner removably attached to the at least one attachment strip opposite the substrate, the first substrate including indica thereon in the form of attachment instructions for the placement of the at least one attachment strip on the C-arm:

b. removing the at least one release liner from the at least one attachment strip; and c. placing the at least one attachment strip on the C-arm where indicated by the indica.

16. The method of claim 15, wherein the indica comprises:

a. a location image of the C-arm; and b. a location icon identifying a location on the C-arm within the location image for proper placement of the at least one attachment strip, wherein the step of placing the at least one attachment strip on the C-arm comprises placing the at least one attachment strip on the C-arm in the location identified by the location icon in the location image of the C-arm in the indica.

17. The method of claim 15, wherein the at least one drape comprises:

a. a plurality of attachment strips disposed on the substrate; and b. a plurality of release liners removably attached to the plurality of attachment strips opposite the substrate, each of the plurality of release liners including indica thereon in the form of attachment instructions for the placement of the associated attachment strip on the C-arm, and wherein the step of placing the at least one attachment strip on the C-arm comprises:

i. removing a first release liner from a first attachment strip;

ii. placing the first attachment strip on the C-arm where indicated by the indicia;

iii. removing a second release liner from a second attachment strip; and iv. placing the second attachment strip on the C-arm where indicated by the indicia.

18. The method of claim 15, wherein the at least one drape comprises:

a. a first drape comprising:

i. a substrate;

ii. at least one attachment strip disposed on the substrate; and iii. at least one release liner removably attached to the at least one attachment strip opposite the substrate, the at least one release liner including first indica thereon in the form of attachment instructions for the placement of the at least one attachment strip on the C-arm; and b. a second drape comprising:

i. a substrate;

ii. at least one attachment strip disposed on the substrate; and iii. at least one release liner removably attached to the at least one attachment strip opposite the substrate, the at least one release liner including second indica thereon in the form of attachment instructions for the placement of the at least one attachment strip on the C-arm; and wherein the method comprises the steps of:

a. removing the at least one release liner from the at least one attachment strip on the first drape;

b. placing the at least one attachment strip on the first drape on the C-arm where indicated by the first indicia;

c. removing the at least one release liner from the at least one attachment strip on the second drape;

d. placing the at least one attachment strip on the second drape on the C-arm where indicated by the second indicia.

* * * * *